US012728109B2

(12) United States Patent
Pham et al.

(10) Patent No.: US 12,728,109 B2
(45) **Date of Patent: *Sep. 8, 2026**

(54) **METHOD OF INCREASING THE POPULATION OF *DIALISTER* SPP. IN THE GUT MICROBIOME**

(71) Applicant: DSM IP ASSETS B.V., Heerlen (NL)

(72) Inventors: Thanh-Van Pham, Kaiseraugst (CH); Ateequr Rehman, Kaiseraugst (CH); Nicole Seifert, Kaiseraugst (CH); Robert Steinert, Kaiseraugst (CH); Wilbert Sybesma, Kaiseraugst (CH)

(73) Assignee: DSM IP ASSETS B.V., Maastricht (NL)

( * ) Notice: Subject to any disclaimer, the term of this patent is extended or adjusted under 35 U.S.C. 154(b) by 697 days.

This patent is subject to a terminal disclaimer.

(21) Appl. No.: 18/014,780

(22) PCT Filed: Jul. 8, 2021

(86) PCT No.: PCT/EP2021/068935

§ 371 (c)(1), (2) Date: Jan. 6, 2023

(87) PCT Pub. No.: WO2022/008633

PCT Pub. Date: Jan. 13, 2022

(65) Prior Publication Data

US 2023/0270705 A1 Aug. 31, 2023

(30) Foreign Application Priority Data

Jul. 9, 2020 (EP) .................................... 20184914

(51) Int. Cl.

| | |
|---|---|
| ***A61K 31/202*** | (2006.01) |
| ***A61K 31/015*** | (2006.01) |
| ***A61K 31/07*** | (2006.01) |
| ***A61K 31/122*** | (2006.01) |
| ***A61K 31/197*** | (2006.01) |
| ***A61K 31/375*** | (2006.01) |
| ***A61K 31/525*** | (2006.01) |
| ***A61K 31/593*** | (2006.01) |
| ***A61P 1/00*** | (2006.01) |

(52) U.S. Cl.

CPC .......... *A61K 31/202* (2013.01); *A61K 31/015* (2013.01); *A61K 31/07* (2013.01); *A61K 31/122* (2013.01); *A61K 31/197* (2013.01); *A61K 31/375* (2013.01); *A61K 31/525* (2013.01); *A61K 31/593* (2013.01); *A61P 1/00* (2018.01)

(58) Field of Classification Search

CPC .. A61K 2300/00; A61K 31/015; A61K 31/07; A61K 31/122; A61K 31/197; A61K 31/202; A61K 31/375; A61K 31/525; A61K 31/593; A61P 1/00; A61P 1/16; A61P 11/06; A61P 25/00; A61P 25/28; A61P 29/00; A61P 3/04; A61P 3/10; A61P 37/08

See application file for complete search history.

(56) References Cited

U.S. PATENT DOCUMENTS

| | | | | |
|---|---|---|---|---|
| 2006/0251722 | A1 * | 11/2006 | Bandak ................ | A61K 9/2081 424/472 |
| 2008/0213239 | A1 | 9/2008 | Morris | |
| 2022/0312816 | A1 * | 10/2022 | Speckmann ......... | A23C 19/093 |

FOREIGN PATENT DOCUMENTS

| | | | | | |
|---|---|---|---|---|---|
| CN | 1522143 | A | | 8/2004 | |
| CN | 105543385 | | * | 5/2016 | |
| EP | 3 539 560 | | | 9/2019 | |
| WO | 02/096408 | | | 12/2002 | |
| WO | 02/096408 | A1 | | 12/2002 | |
| WO | 2017/220802 | | | 12/2017 | |
| WO | WO-2020043797 | A1 | * | 3/2020 | ......... A61K 31/4188 |

OTHER PUBLICATIONS

WebMD, 2025, https://www.webmd.com/add-adhd/childhood-adhd/preventing-adhd (Year: 2025).*

MayoClinic, 2025, https://www.mayoclinic.org/diseases-conditions/autism-spectrum-disorder/symptoms-causes/syc-20352928 (Year: 2025).*

Healthline, 2025, https://www.healthline.com/health/multiple-sclerosis-prevention (Year: 2025).*

Who—2025 (https://www.who.int/tools/elena/review-summaries/vitamina-neonatal--vitamin-a-supplementation-for-the-prevention-of-morbidity-and-mortality-in-infants-one-to-six-months-of-age, 2025) (Year: 2025).*

Arthritis Foundation, 2021, https://www.arthritis.org/health-wellness/about-arthritis/understanding-arthritis/reduce-your-risk (Year: 2021).*

Kanhere, J Clin Endocrinol Metab, Feb. 2018, 564-574 (Year: 2018).*

Bloch, Clin Adolesc Psychiartr Clin N Am 2014 (Year: 2014).*

Imdad, 2016, Cochrane Library (Year: 2016).*

Khan et al. (Pathogens, 2019, p. 1-28) (Year: 2019).*

International Search Report for PCT/EP2021/068935, mailed Sep. 27, 2021, 3 pages.

(Continued)

*Primary Examiner* — Umamaheswari Ramachandran

(74) *Attorney, Agent, or Firm* — NIXON & VANDERHYE P.C.

(57) ABSTRACT

The population of *Dialister* spp. bacteria in the gut microbiome is lower in people with various diseases. We have found that administration of vitamins/vitamin combinations such as: beta-carotene, Vitamin A, Vitamin D, Vitamin B5, Vitamin B2, a combination of Vitamin B2 and Vitamin C, Vitamin K, DHA, or EPA, when administered directly to the large intestine, so that it provides nourishment to the gut microbiome directly, can result in an increase of *Dialister* spp.

2 Claims, 1 Drawing Sheet

(56) References Cited

OTHER PUBLICATIONS

Written Opinion of the ISA for PCT/EP2021/068935, mailed Sep. 2021, 5 Pages.

Bansal, Vipin et al., *Novel Perspective in Colon Specific Drug Delivery System*, Polymers in Medicine, 2014, 44, 2, 109-118.

* cited by examiner

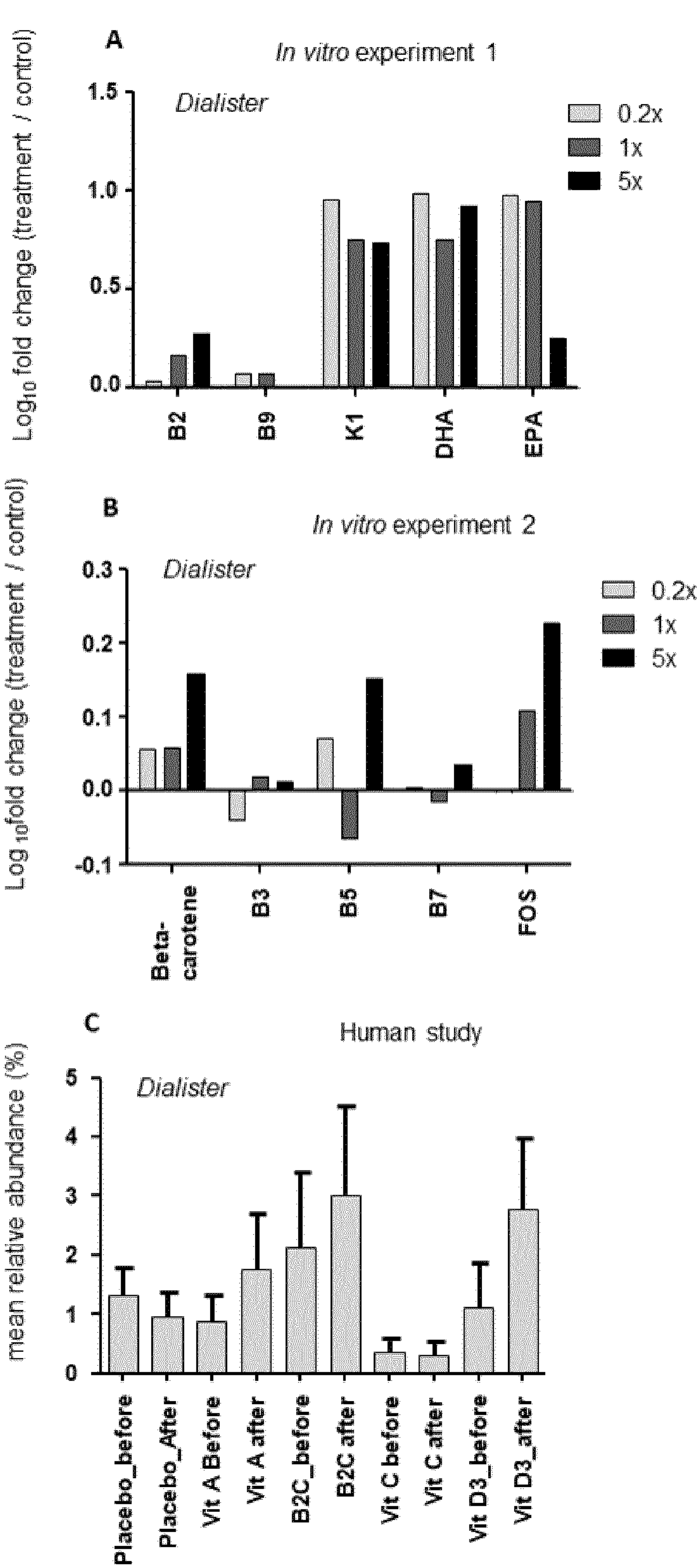
A
In vitro experiment 1
Dialister
0.2x
1x
5x
Log10 fold change (treatment / control)
1.5
1.0
0.5
0.0
B2
B9
K1
DHA
EPA
B
In vitro experiment 2
Dialister
0.2x
1x
5x
Log10fold change (treatment / control)
0.3
0.2
0.1
0.0
-0.1
Beta-carotene
B3
B5
B7
FOS
C
Human study
Dialister
mean relative abundance (%)
5
4
3
2
1
0
Placebo_before
Placebo_After
Vit A Before
Vit A after
B2C_before
B2C after
Vit C before
Vit C after
Vit D3_before
Vit D3_after

METHOD OF INCREASING THE POPULATION OF *DIALISTER* SPP. IN THE GUT MICROBIOME

This application is the U.S. national phase of International Application No. PCT/EP2021/068935 filed Jul. 8, 2021 which designated the U.S. and claims priority to EP 20184914.8 filed Jul. 9, 2020, the entire contents of each of which are hereby incorporated by reference.

BRIEF DESCRIPTION OF THE INVENTION

This invention relates to methods of increasing the gut microbiome population of *Dialister* spp., by delivering vitamins or combinations of vitamins directly to the gut microbiome of an animal, preferably a human. This can be accomplished by using, for example a delayed release formulation of the chosen vitamin or PUFA, preferably beta-carotene, Vitamin A, Vitamin D, Vitamin B5, Vitamin B2, a combination of Vitamin B2 and Vitamin C, Vitamin K, DHA, EPA, and a combination of EPA and DHA.

BACKGROUND OF THE INVENTION

*Dialister* is a genus of bacteria found in the gut microbiome and includes *D. pneumosintes, D. invisus, D. micraerophilus, D. hominis, D. massiliensis, D. succinatiphilus* and *D. propionicifaciens* found in the gut microbiome. Previously *D. pneumosintes* was known as *Bacteroides pneumosintes*.

Studies have shown that a lower than normal amount of *Dialister* spp. in the gut is associated with various seemingly unrelated disease states and/or adverse conditions. These include: irritable bowel syndrome, autism spectrum disorder, impaired calcium absorption, food allergies and sensitization (milk, eggs, peanuts, soy, walnut, and wheat), generalized anxiety disorder, childhood obesity, impaired growth and morbidity of infants, immune-mediated inflammatory disease; atopic disorders (including asthma and allergies in children), Crohn's Disease, rheumatoid arthritis and osteoarthritis, early-onset preeclampsia, Type 1 Diabetes, juvenile idiopathic arthritis, depression, attention-deficit hyperactive disorder (ADHD), chronic hepatitis B, major depressive disorder, airway allergy, multiple sclerosis, chronic inflammation, and Alzheimer's disease.

It would be desirable to provide a method to increase the population of *Dialister* spp. in the gut microbiome, particularly in individuals which are experiencing or at risk on experiencing one of the aforementioned diseases/adverse conditions or symptoms associated with one of the diseases/adverse conditions.

DETAILED DESCRIPTION ON THE INVENTION

A large number of studies have shown that the population of *Dialister* spp. in the gut microbiome is decreased when an animal, preferably a human, is suffering from a particular disease/adverse condition compared to the population present in the animal not suffering that particular disease/adverse condition. However, none of these studies have suggested a method of how to increase the population of *Dialister* spp., thus alleviating at least one of the symptoms of the disease/adverse condition. It has been found, in accordance with this invention, that direct delivery of certain vitamins or polyunsaturated fatty acids ("PUFAs") to the large intestine of an animal, preferably a human, can provide nourishment to the gut microbiome, and increase the resident population of *Dialister* spp. Thus, this invention relates to methods of prevention, reducing the risk or delaying the onset of a disease/adverse condition, and/or treatment of a disease/adverse condition which is characterized in a lower than normal population of *Dialister* spp. in the gut microbiome, by administering at least one vitamin or PUFA which is delivered directly into the intestine.

In accordance with the invention, we have found that certain vitamins and PUFAs are suitable for increasing the population of *Dialister* spp. in the gut, which, when made available to the gut microbiome, are selected from the group consisting of: beta-carotene, Vitamin A, Vitamin D, Vitamin B5, Vitamin B2, a combination of Vitamin B2 and Vitamin C, Vitamin K, docosahexaenoic acid "DHA", eicosapentaenoic acid "EPA", and a combination of EPA and DHA.

Thus one aspect of this invention is a method of increasing the population of *Dialister* spp. in the gut microbiome comprising administering a population-increasing effective amount of a vitamin or PUFA selected from the group consisting of beta-carotene, Vitamin A, Vitamin D, Vitamin B5, Vitamin B2, a combination of Vitamin B2 and Vitamin C, Vitamin K, DHA, EPA, and a combination of EPA and DHA; directly to the large intestine of an animal, preferably a human.

Another embodiment of this invention is the treatment and or prevention of a disease or adverse condition which is associated with a decreased population of *Dialister* spp. in the gut microbiome, comprising administering a vitamin or PUFA selected from the group consisting of: beta-carotene, Vitamin A, Vitamin D, Vitamin B5, Vitamin B2, a combination of Vitamin B2 and Vitamin C, Vitamin K, DHA, EPA, and a combination of EPA and DHA directly to the large intestine of an animal, preferably a human in need thereof. Conditions or diseases which are characterized by a decreased population of *Dialister* spp. include: irritable bowel syndrome, autism spectrum disorder, impaired calcium absorption, food allergies and sensitization (milk, eggs, peanuts, soy, walnut, and wheat), generalized anxiety disorder, childhood obesity, impaired growth and morbidity of infants, immune-mediated inflammatory disease; atopic disorders (including asthma and allergies in children), Crohn's Disease, rheumatoid arthritis and osteoarthritis, early-onset preeclampsia, Type 1 Diabetes, juvenile idiopathic arthritis, depression, attention-deficit hyperactive disorder (ADHD), chronic hepatitis B, major depressive disorder, airway allergy, multiple sclerosis, chronic inflammation, and Alzheimer's disease.

Another embodiment of this invention is an oral delivery formulation comprising a *Dialister* spp. population increasing effective amount of a vitamin or PUFA selected from the group of consisting of beta-carotene, Vitamin A, Vitamin D, Vitamin B5, Vitamin B2, a combination of Vitamin B2 and Vitamin C, Vitamin K, DHA, EPA, and a combination of EPA and DHA; and excipients and said form is characterized in that the vitamin or PUFA is delivered to the gut microbiome in the large intestine.

Another embodiment of this invention is a medical food which addresses the nutritional needs of a patient experiencing at least one symptom of a disease/adverse condition selected from the group consisting of: irritable bowel syndrome, autism spectrum disorder, impaired calcium absorption, food allergies and sensitization (milk, eggs, peanuts, soy, walnut, and wheat), generalized anxiety disorder, childhood obesity, impaired growth and morbidity of infants, immune-mediated inflammatory disease; atopic disorders (including asthma and allergies in children), Crohn's Disease, rheumatoid arthritis and osteoarthritis, early-onset preecampsia, Type 1 Diabetes, juvenile idiopathic arthritis, depression, attention-deficit hyperactive disorder (ADHD), chronic hepatitis B, major depressive disorder, airway allergy, multiple sclerosis, chronic inflammation, and Alzheimer's disease; comprising a nutrient selected from the group consisting of: beta-carotene, Vitamin A, Vitamin D, Vitamin B5, Vitamin B2, a combination of Vitamin B2 and Vitamin C, Vitamin K, DHA, EPA, and a combination of EPA and DHA, characterized in that the nutrient is formulated for direct delivery to the gut microbiome.

Definitions

As used throughout the specification and claims, the following definitions apply:

"*Dialister* spp." means at least one species of the genus *Dialister*, and may include *D. pneumosintes, D. invisus, D. micraerophilus, D. hominis, D. massiliensis, D. succinatiphilus* and *D. propionicifaciens.*

"Decreased population" means that the amount of *Dialister* spp. present in the individual is lower compared to than that found in a healthy population of people.

"Healthy" as used herein means the animal, including a human is not experiencing a disease/adverse condition which is known to be associated with a decreased population of *Dialister* spp. in the gut microbiome.

The terms "Vitamin B2" and "riboflavin" are used interchangeably, and include their esters, and in particular riboflavin-5'-phosphate.

The term "Vitamin K" includes either or both of Vitamin K1 and Vitamin K2.

"DHA" includes the free acid forms thereof as well as salts and esters, such as ethyl esters. It also includes various concentrations, including at least 90% pure. It also includes fish oils and algal oils which contain DHA, either in naturally occurring amounts or in concentrated amounts, and may also include EPA. It further includes DHA triglycerides.

"EPA" includes the free acid forms thereof as well as salts and esters thereof. It also includes varying concentrations, including at least 90% pure. It also includes fish oils and algal oils which can contain EPA in some amount, and may also include DHA. Further it includes EPA triglycerides.

The term "Vitamin D" as used herein means vitamin D3. 25-hydroxyvitamin D3 can be use in lieu of or in addition to Vitamin D3, preferably in non-human species. The relative strength of 25-hydroxyvitamin D3 to Vitamin D3 is approximately 40:1, so dosing of 25-hydroxyvitamin D3 should be adjusted accordingly.

An animal, preferably a human "in need of having their population of *Dialister* spp. increased" is at risk of, or is currently experiencing at least one disease/adverse condition selected from the group consisting of: irritable bowel syndrome, autism spectrum disorder, impaired calcium absorption, food allergies and sensitization (milk, eggs, peanuts, soy, walnut, and wheat), generalized anxiety disorder, childhood obesity, impaired growth and morbidity of infants, immune-mediated inflammatory disease; atopic disorders (including asthma and allergies in children), Crohn's Disease, rheumatoid arthritis and osteoarthritis, early-onset preeclampsia, Type 1 Diabetes, juvenile idiopathic arthritis, depression, attention-deficit hyperactive disorder (ADHD), chronic hepatitis B, major depressive disorder, airway allergy, multiple sclerosis, chronic inflammation, and Alzheimer's disease.

"Prevention" is not limited to the state where a disease/adverse condition is never achieved. Instead, as used throughout the specification and claims, it can include lessening the severity of a disease/adverse condition, or a symptom thereof; delayed onset of a disease/adverse condition, or a symptom thereof; early intervention in a disease/adverse condition or symptom thereof; and lessening the risk of development of a disease/adverse condition, or symptom.

"Direct delivery" means that the vitamin or PUFA is administered in a manner such that the vitamin or PUFA is not absorbed in the stomach and/or small intestine; rather the vitamin and/or combination becomes present in the distal intestinal tract, preferably the large intestine, where it is available to the microbiome. These vitamins or PUFAs are not part of a person's usual daily nutritional requirements (generally obtained through diet and conventional vitamin or PUFA supplementation), and are administered in excess thereof. For human use, the preferred method is through a form which delays delivery until the intestinal tract is reached. For non-human animals, a preferred delivery includes a method of administering a large enough dose so that only a portion of the vitamin or PUFA delivered is absorbed in the stomach, and the remainder, which is an effective dose, is available to the intestinal tract; although not preferred, this method of delivery can be used for humans as well.

BRIEF DESCRIPTION OF THE FIGURES

FIG. 1. Relative abundance of *Dialister* upon administration of vitamins in in vitro experiment 1 (A), in in vitro experiment 2 (B) and in human study (C). FIGS. 1A and 1B shows log 10 fold changes of *Dialister* abundances in comparison to control in fermentation supernatant at 24 h. FIG. 1C shows relative abundance of fecal *Dialister* upon administration of colon-targeted vitamins in human study.

DISEASES/ADVERSE CONDITIONS

Another embodiment of this invention is the use of a PUFA or vitamin formulated for direct delivery to the gut microbiome of an animal, preferably a human, and characterized in that upon delivery, it increases the population of *Dialister* spp. in the gut microbiome. Preferably the vitamin and/or vitamin combination is selected from the group consisting of: beta-carotene, Vitamin A, Vitamin D, Vitamin B5, Vitamin B2, a combination of Vitamin B2 and Vitamin C, Vitamin K, DHA, EPA, and a combination of EPA and DHA. In some embodiments the animal, including a human who is in need of increasing the population of *Dialister* spp. is at risk for or experiencing a disease or condition selected from the group consisting of: irritable bowel syndrome, autism spectrum disorder, impaired calcium absorption, food allergies and sensitization (milk, eggs, peanuts, soy, walnut, and wheat), generalized anxiety disorder, childhood obesity, impaired growth and morbidity of infants, immune-mediated inflammatory disease; atopic disorders (including asthma and allergies in children), Crohn's Disease, rheumatoid arthritis and osteoarthritis, early-onset preeclampsia, Type 1 Diabetes, juvenile idiopathic arthritis, depression, attention-deficit hyperactive disorder (ADHD), chronic hepatitis B, major depressive disorder, airway allergy, multiple sclerosis, chronic inflammation, and Alzheimer's disease; and the population of *Dialister* spp. is increased by administering a vitamin or PUFA selected from the group consisting of: beta-carotene, Vitamin A, Vitamin D, Vitamin B5, Vitamin B2, a combination of Vitamin B2 and Vitamin C, Vitamin K, DHA, EPA, and a combination of EPA and DHA.

Another embodiment of this invention the non-therapeutic use of a PUFA and/or a vitamin formulated for direct delivery to the gut microbiome and characterized in that upon delivery, it increases the population of *Dialister* spp. in the gut microbiome of an animal preferably a human. Preferably the PUFA or vitamin is selected from the group consisting of: beta-carotene, Vitamin A, Vitamin D, Vitamin B5, Vitamin B2, a combination of Vitamin B2 and Vitamin C, Vitamin K, DHA, EPA, and a combination of EPA and DHA.

Another embodiment of this invention is the use of a vitamin or PUFA combination in the manufacture of a medicament formulated for direct delivery and characterized that upon delivery, it increases the population of *Dialister* spp. in the gut microbiome of an animal preferably a human. Preferably the PUFA or vitamin is selected from the group consisting of: beta-carotene, Vitamin A, Vitamin D, Vitamin B5, Vitamin B2, a combination of Vitamin B2 and Vitamin C, Vitamin K, DHA, EPA, and a combination of EPA and DHA.

In some embodiments the PUFA or vitamin will be used to increase the population of *Dialister* spp. in an animal or person at risk for, or experiencing a disease or condition selected from the group consisting of: irritable bowel syndrome, autism spectrum disorder, impaired calcium absorption, food allergies and sensitization (milk, eggs, peanuts, soy, walnut, and wheat), generalized anxiety disorder, childhood obesity, impaired growth and morbidity of infants, immune-mediated inflammatory disease; atopic disorders (including asthma and allergies in children), Crohn's Disease, rheumatoid arthritis and osteoarthritis, early-onset preeclampsia, Type 1 Diabetes, juvenile idiopathic arthritis, depression, attention-deficit hyperactive disorder (ADHD), chronic hepatitis B, major depressive disorder, airway allergy, multiple sclerosis, chronic inflammation, and Alzheimer's disease; by administering a vitamin or vitamin combination selected from the group consisting of: beta-carotene, Vitamin A, Vitamin D, Vitamin B5, Vitamin B2, a combination of Vitamin B2 and Vitamin C, Vitamin K, DHA, EPA, and a combination of EPA and DHA.

The aforementioned vitamins and combinations of vitamins may be administered as a sole active agent(s), or may be administered in combination with conventionally used prebiotics, probiotics, other ingredients which may modulate the gut microbiome, and conventional pharmaceutical or nutritional agents. Thus, DHA may be chosen as a sole active agent; EPA may be chosen as a sole active agent; Vitamin K may be chosen as a sole active agent; beta-carotene may be the sole active agent; Vitamin A may be the sole active agent; Vitamin D may be the sole active agent, Vitamin B5 may be the sole active agent, Vitamin B2 may be the sole active agent, a combination of Vitamin B2 and Vitamin C may be the sole active agents; or a combination of EPA and DHA may be the sole active agents.

Animals

"Animals" include mammals, poultry and preferably humans. Preferred non-human animals are companion animals, and include as dogs, cats, and horses. Among agriculturally important animals, preferred animals include poultry, swine, bovines, ovines and caprines and equines.

Dosages

The dosages used herein are intended to be in addition to the active ingredient that is ingested for general nutrition purposes. Instead, they act upon the gut microbiome environment as a whole, at the genus, species and strain level of the gut microbes. The active agents are not intended to be metabolized directly by the animal, including the human. Rather they are intended to be utilized by the bacterial population of the colon. Therefore, the amounts reported below would be consumed by the animal in addition to the usual diet, but as they are not directly available to the animal due to their delayed release.

Suitable dosages per day are:

Riboflavin: up to 200 mg per day; preferably 1-85 mg per day; more preferably 70-80 mg per day. In one embodiment about 75 mg per day are used. Preferably, riboflavin is administered in an amount such that its local concentration in the colon is at least 0.05 g/L, preferably at least 0.1 g/L more preferably at 0.125 g/L. Preferred local concentrations in the colon range from about 0.1 g/L to about 0.5 g/L or from about 0.1 g/L to about 0.2 g/L, preferably about 0.125 g/L. One preferred dosage per day can be up to 200 mg.

Beta Carotene: up to 150 mg per day (add range). Preferably, β-carotene is administered in an amount such that its local concentration in the colon is at least 0.1 g/L, preferably at least 0.15 g/L, most preferably at least 0.2 g/L. Preferred local concentrations in the colon range from about 0.05 g/L to about 0.4 g/L, more preferably from about 0.15 g/L to about 0.25 g/L. One preferred dosage per day is up to 150 mg.

Vitamin B5: up to 1500 mg per day (add range). Preferably, vitamin B5 is administered in an amount such that its local concentration in the colon is at least 1 g/L, preferably at least 1.5 g/L, most preferably at least 2 g/L. Preferred local concentrations in the colon range from about 0.5 g/L to about 4 g/L, more preferably from about 1.5 g/L to about 2.5 g/L One preferred dosage per day is up to 1500 mg.

Vitamin C: up to 2000 mg per day; preferably 400-600 mg per day; more preferably 450-550 mg per day. Preferably, ascorbic acid is administered in an amount such that its local concentration in the colon is at least 0.05 g/L, preferably at least 0.1 g/L, most preferably at least 0.8 g/L. Preferred local concentrations in the colon range from about 0.05 g/L to about 1.5 g/L, more preferably from about 0.5 g/L to about 1 g/L, most preferably from about 0.8 g/L to about 0.9 g/L. One preferred dosage per day is up to 2000 mg.

Vitamin D3: up to 250 micrograms per day; preferably 5-80 micrograms per day; more preferably 15-25 micrograms per day.

Vitamin K: up to 10,000 micrograms per day, preferably 80-140 micrograms per day, more preferably 100-120 micrograms per day. In one embodiment 110 micrograms are given per day Combined DHA and EPA: up to 5,000 mg per day. The ratio of DHA to EPA is not critical. In one embodiment the ratio of EPA to DHA may be the same as that occurring in natural fish oil or algal oil combinations. Other non-limiting ratios which may be provided include DHA to EPA 10-1: 1-10.

DHA: up to 1000 mg per day; preferably 80-120 mg per day; more preferably 90-110 mg. In one embodiment about 100 mg are used.

EPA up to 1800 mg per day preferably 80-120 mg per day; more preferably 90-110 mg per day; In one embodiment about 100 mg per day are used.

For the combination of Vitamins B2 and C, the ratio of Vitamin B2 to C is not critical. Generally the amount of Vitamin C is much higher than the amount of B2, for example 500 mg to 1000 mg Vitamin C and 1 mg Vitamin B2.

For direct delivery using delayed release formulations, dosages are preferably taken once per day, but may be taken in multiple smaller doses (i.e. two half-doses per day or three ⅓ does per day) if desired.

For dosages which are to be administered as a high dose rather than direct delivery to the gut, as would be common if the animal is non-human, the amount may be at least about 10× or even 20× the recommended dose, for example if the recommended daily dose is 5 mg, the amount, preferably administered in the food, form or feed, is 50 mg or 100 mg in order for the vitamins and/or PUFAs to be present in the colon. For humans, the dosage may need to be adjusted higher.

It is preferred that the doses be taken for a sustained period of time, for example, at least one week, preferably at least 2 weeks, and more preferably at least one month. Doses may be taken for daily over a sustained period of time if desired.

Formulations

A suitable formulation may include a high enough dosage so that a portion of the some of the vitamin/PUFAs are absorbed normally, but the remainder is available to the gut microbiome in the intestine at an effective amount. Other formulations include non-oral routes, such as via suppositories or injections. Preferred formulations are delayed release oral formulations.

A used herein, "delayed release" refers to the release of the active agent at a time later than immediately after administration. Preferably, "delayed release" means delivery of the active agent, upon oral administration, to the large intestine, preferably the colon, in a delayed manner relative to an immediate release formulation.

An "enteric layer" is a layer surrounding a core, wherein the core comprises the active agent and the layer confers resistance to gastric juice. An "enteric shell" is a shell or matrix surrounding or encapsulating the active agent, wherein the shell confers resistance to gastric juice. Alternatively, a matrix-based delivery system can be used. Matrix based systems have no discrete layer of coating material but the active agent is more or less homogeneously distributed within the matrix. Further, there are colon-release systems that embed the active agent in e.g. in a fiber matrix (enzyme-triggered) and an enteric coating on top.

In a preferred embodiment for humans, the formulation of the present invention is a solid dosage form for oral administration. The formulation may be in the form of a capsule, pellet, bead, sphere, mini spheres, tablet, mini tablet, or granule, optionally coated with a delayed release coating or shell that prevents the release of the active agent before the small intestine, preferably before the colon.

Coating, shell, or matrix materials for the delayed release of the active agent, in particular for targeted release in the ileum or the large intestine, upon oral administration are known in the art. They can be subdivided into coating materials that disintegrate above a specific pH, coating materials that disintegrate after a specific residence time in the gastrointestinal tract and coating materials that disintegrate due enzymatic triggers specific to the microflora of a specific region of the intestines. Coating or shell materials from different categories are commonly used in combinations. Coating or shell materials of these three different categories for targeting to the large intestine have been reviewed for example in Bansal et al. (Polim. Med. 2014, 44, 2, 109-118). In one embodiment of the present invention the delayed release coating comprises at least one component selected from coating materials that disintegrate pH-dependently, coating materials that disintegrate time-dependently, coating materials that disintegrate due to enzymatic triggers in the intestinal environment (e.g. in the intestinal environment of the ileum and the large intestine), and combinations thereof.

Coating materials that disintegrate pH-dependently include polyvinyl acetate phthalate, cellulose acetate trimellitate, hydroxypropyl methylcellulose phthalate HP-50, HP-55 or HP-55S, cellulose acetate phthalate, shellac, hydroxypropyl methylcellulose acetate succinate (HPMCAS), poly(methacrylic acid, ethyl acrylate) 1:1 (Eudragit® L100-55, Eudragit® L30D-55), poly(methacrylic acid, methyl methacrylate) 1:1 (Eudragit® L-100, Eudragit® L12.5), poly(methacrylic acid, methyl methacrylate) 1:2 (Eudragit® S-100, Eudragit® S12,5, and Eudragit® FS30D).

Coating materials that disintegrate time-dependently include Eudragit® RL, Eudragit® RS, and ethylcellulose.

Coating materials that disintegrate due to enzymatic triggers in the large intestinal environment include chondroitin sulfate, pectin, guar gum, chitosan, inulin, lactulose, raffinose, stachyose, alginate, dextran, xanthan gum, locust bean gum, arabinogalactan, cyclodextrin, pullulan, carrageenan, scleroglucan, chitin, curdulan, levan, amylopectin, starch, amylose, resistant starch, and azo compounds being degraded by azo bonds splitting bacteria.

In one embodiment the formulation comprises an enteric capsule, filled with a composition comprising the active agent. The enteric capsule confers resistance against the acidic environment of the stomach. For example, softgel formulations may deliver the active agent in solution and yet offer advantages of solid dosage forms. Softgel capsules are particularly suited for hydrophobic active agents which do not dissolve readily in water. Vitamin K and omega-3 fatty acids are preferably formulated in softgel capsules.

In another embodiment, the formulation is a tablet comprising (i) a core comprising the active agent, and (ii) a delayed release coating such as an enteric coating. This may be a hard gel capsule.

The release of the active agent may be delayed until small intestine. In another embodiment, the release of the active agent(s) is delayed until the distal small intestine. In yet another embodiment, the release of the active agent(s) is delayed until the colon.

The following non-limiting Examples better illustrate the invention.

EXAMPLES

Example 1

In Vitro Fermentation Study 1

Donors and Sample Preparation

At the start of this intestinal batch fermentation incubation, all test ingredients were added from stock solutions to the modified nutritional medium, containing (g/l): 2.5 $K_2HPO_4$, 10.9 $KH_2PO_4$, 2 $NaHCO_3$, 2 yeast extract, 2 peptone, 1 mucin, 0.5 cysteine, 2 Tween 80, 2 glucose, 2 starch, 2 cellobiose, 0.1 NaCl, 0.01 $MgSO_4 \cdot 7H_2O$, 0.01 $CaCl_2 \cdot 6H_2O$, 0.05 hemin, 0.5 bile salts.

The following compounds were added from stock solutions prepared in water for vitamin B2 and B9, and in ethanol for vitamin K1, DHA and EPA:

TABLE 1

Dose designation and final concentration of micronutrients in in vitro fermentation experiment 1

| | Dose | Final concentration |
|---|---|---|
| Vitamin B2 (Riboflavin) | 0.2x | 0.06 mg/ml |
| | 1x | 0.29 mg/ml |
| | 5x | 1.43 mg/ml |
| Vitamin B9 (Folic acid) | 0.2x | 0.29 μg/ml |
| | 1x | 1.43 μg/ml |
| | 5x | 7.14 μg/ml |
| Vitamin K1 | 0.2x | 0.01 μg/ml |
| | 1x | 0.04 μg/ml |
| | 5x | 0.18 μg/ml |
| DHA | 0.2x | 0.11 mg/ml |
| | 1x | 0.54 mg/ml |
| | 5x | 2.68 mg/ml |
| EPA | 0.2x | 1.29 mg/ml |
| | 1x | 6.43 mg/ml |
| | 5x | 32.14 mg/ml |

Each compound was tested in three different concentrations. As a source of the microbial community, freshly prepared fecal suspension from a donor was added to the reactors. Each reactor had a volume of 70 ml. All tests, except the blanks, were performed in single repetition. Incubation conditions were 48 h at 37° C., under shaking (90 rpm) and anaerobic conditions.

Measurements

Microbial composition: Total DNA was extracted from all fermentation samples collected throughout the study using the QIAamp DNA stool minikit (Qiagen, Crawley, United Kingdom) according to the manufacturer's instructions, apart from addition of a bead-beating step and increasing the lysis temperature to 95° C. as described previously. After DNA isolation, DNA was quantified using the Qubit High Sensitivity DNA assay (Thermo Fisher). Whole metagenome libraries were then prepared using the Illumina Nextera XT kit (Illumina) in accordance with the manufacturer's instructions, with the following modifications: Firstly, tagmentation time was increased to 7 min and secondly, following incorporation of indices and Ampure purification of the products, the samples were each individually sized by running on an Agilent High Sensitivity Chip (Agilent) and quantified using the Qubit High Sensitivity DNA assay (Thermo Fisher) in accordance with Teagasc Sequencing Platform SOPs. The samples were then pooled equimolarly and sequenced on the Illumina NextSeq 500 with a NextSeq 500/550 v 2 high-output reagent kit (300 cycles). All sequencing was done in the Teagasc sequencing facility in accordance with standard Illumina sequencing protocols. Delivered raw FASTQ sequence files were quality checked as follows: poor quality and duplicate read removal, as well as trimming was implemented using a combination of SAM and Picard tools. Taxonomy was assigned to the reads using the Metaphlan2 software.

Example 2

In Vitro Fermentation Study 2

Donors and Sample Preparation

At the start of this intestinal batch fermentation incubation, all test ingredients were added from stock solutions to the modified nutritional medium, containing (g/l): 2.5 K2HPO4, 10.9 KH2PO4, 2 NaHCO3, 2 yeast extract, 2 peptone, 1 mucin, 0.5 cystein, 2 Tween 80, 2 glucose, 2 starch, 2 cellobiose, 0.1 NaCl, 0.01 MgSO4·7H2O, 0.01 CaCl2·6H2O, 0.05 hemin, 0.5 bile salts.

The following compounds were added from stock solutions prepared in water:

Beta-carotene,

Vitamin B3,

Vitamin B5,

Vitamin B7,

Fructooligosaccharides (positive control)

Each compound was tested in three different concentrations; an overview is given in Table 2, below. As a source of the microbial community, freshly prepared fecal suspension from a donor was added to the reactors. Each reactor had a volume of 70 ml. All tests, except the blanks, were performed in single repetition. Incubation conditions were 48 h at 37° C., under shaking (90 rpm) and anaerobic conditions.

TABLE 2

Dose designation and final concentration of micronutrients in in vitro fermentation experiment 2

| | Dose | Final concentration |
|---|---|---|
| Beta-carotene | 0.2x | 0.048 mg/ml |
| | 1x | 0.24 mg/ml |
| | 5x | 1.2 mg/ml |
| Vitamin B3 (Niacinamide) | 0.2x | 0.002625 mg/ml |
| | 1x | 0.013125 mg/ml |
| | 5x | 0.065625 mg/ml |
| Vitamin B5 (Pantothenic acid) | 0.2x | 0.45 mg/ml |
| | 1x | 2.25 mg/ml |
| | 5x | 11.25 mg/ml |
| Vitamin B7 (Biotin) | 0.2x | 5 mg/ml |
| | 1x | 25 mg/ml |
| | 5x | 125 mg/ml |
| Fructooligosaccharide (FOS) | 0.5x | 0.5 mg/ml |
| | 1x | 1 mg/ml |
| | 2x | 2 mg/ml |

Measurements

Microbial composition: Illumina sequencing was performed at the start and after 24 h of incubation. The technique targets the 16S rRNA gene that consists of variable and conserved regions, spread over the gene. Due to their key role in protein expression, the conserved regions are characterized by very low evolutionary rates.

The methodology applied involves primers that span 2 hypervariable regions (V3-V4) of the 16S rRNA gene. Using a pair-end sequencing approach, sequencing of 2×250 bp results in 424 bp amplicons. Such fragments are taxonomically more informative as compared to smaller fragments. Samples that were analyzed with Illumina sequencing were also analyzed with flow cytometry to determine the number of total bacterial cells, thus allowing to convert the proportional values obtained with Illumina into absolute quantities. Samples were analyzed on a BDFacs verse. The samples were run using the high flow rate. Bacterial cells were separated from medium debris and signal noise by applying a threshold level of 200 on the SYTO channel. Proper parent and daughter gates were set to determine all populations.

Example 3

Clinical Study

Human Subjects

Twelve participants were allocated to each of the six vitamin groups, and 24 participants allocated to the placebo group. All 96 participants completed the intervention. To be considered eligible for enrollment into the study, participants have to be able to give written informed consent; be aged between 20 and 50 years of age; have a BMI of between 18.5-30 Kg/m2; have a stable body weight (<5% change) over the past 3-months; be in generally good health, as determined by the investigator; have not consumed dietary supplements, prebiotic, probiotic, dietary or fiber-rich supplements within 4 weeks prior to baseline visit and be willing to avoid these supplements until the end of the study; be willing to avoid liver consumption for the duration for the study, be willing to maintain their current level of physical activity for the duration of the study; and be willing to consume the IP daily for the duration of the study. Any participants who have a typical fiber intake>30 g/day; were pregnant or planning to become pregnant, have consumed disallowed medications; had made major dietary changes over the past three months or had planned major lifestyle changes; had taken part in a study within the previous 60 days; or had any ongoing or previous illness that the investigator deemed would impact on the objectives of the study were excluded. The study protocol was approved by the Clinical Research Ethics Committee of the Cork Teaching Hospitals (Protocol Number: AFCRO-087) and performed in accordance with the Declaration of Helsinki. Each subject provided written informed consent before inclusion in the study. The trial was registered with clinicaltrials.gov under the ID: NCT03668964.

Study Design

The trial was a randomized, double-blind, placebo-controlled, parallel study in which subjects received either the vitamin supplement or placebo over four weeks. There were three visits: 1) screening; 2) baseline (one week after screening) and 3) follow-up (four weeks after baseline). At the screening visit (Visit 1), informed consent was obtained, and eligibility was reviewed including a medical history interview and a physical exam. Eligible participants started a one-week run-in period and were instructed to refrain from extreme diets. The participants completed an eDiary daily and collected a fecal sample in the 48 hours prior to their randomization visit. Before the randomization visit, participants food frequency questionnaires were analyzed to ensure their typical fiber intake is <30 g fiber/day. Any participants outside this criterion, or outside any of the other eligibly criteria were excluded.

At the baseline visit (Visit 2), participants retuned a fecal samples collected in the previous 48 hours and eligibility was assessed. Eligible participants were enrolled and allocated a randomization number, and a 4-week supply of investigational product (IP) from one of the seven arms. Both the participant and research staff were blinded to the allocation. Participants completed the GSRS the SF-36 questionnaires. A bloods sample was collected and stored onsite at −80° C. Participants were instructed refrain from extreme diets, complete their eDiary daily, and to consume one capsule daily for the next 4 weeks.

At the final visit (Visit 3) participants retuned a fecal samples collected in the previous 48 hours. Participants completed the GSRS the SF-36 questionnaires. A bloods sample was collected and stored onsite at −80° C. Participants returned their IP and compliance was assessed.

Investigational Products

Investigational products were as follows:

1) vitamin A (250 µg retinol equivalents (RE)/day),
2) vitamin C (500 mg ascorbic acid/day),
3) vitamin B2 (75 mg/day)+vitamin C (500 mg/day),
4) vitamin D3 (60 µg cholecalciferol/day), or
5) 200 mg/day microcrystalline cellulose (placebo).

All vitamins were provided by DSM Nutritional Products Ltd (Kaiseraugst, Switzerland); placebo was obtained from Fagron (Waregem, Belgium). Investigational products were formulated as a colon-release form in hard gelatin capsules (Lonza, Bornem, Belgium) coated using the pH-dependent polymer Eudragit S100 (Evonik Nutrition & Care GmbH, Darmstadt, Germany) that has been validated for targeted colon delivery (Cole et al., 2002). The selected doses were based on high dose oral delivery of vitamins in previous studies (de Vries et al., 2006; Lakoff et al., 2014; Cantarel et al., 2015; Steinert et al., 2016; Tang et al., 2016) subtracting estimated intestinal absorption level for each vitamin (Graf, 1980; Basu and Donaldson, 2003; Gropper et al., 2004; Reboul, 2013). All doses were below the upper limits published by EFSA, except vitamin B2 with no upper limit established (https://www.efsa.europa.eu/sites/default/files/assets/UL_Summary_tables.pdf).

Measurements

Fecal microbial composition: DNA extraction and sequencing was performed using the same method as for fermentation samples of the in vitro fermentation study 1.

Results

In Vitro Experiment 1 (FIG. 1A):

There was no distinct increase in *Dialister* relative abundances with vitamin B9. In contrast, administration of vitamin B2, and particularly vitamin K1 and polyunsaturated fatty acid, EPA and DHA led to a substantial increase in *Dialister* relative abundances at all tested concentrations when compared to control at 24 hours.

In Vitro Experiment 2 (FIG. 1B):

There was no distinct increase in *Dialister* relative abundances with vitamin B3 and B7. In contrast, administration of beta-carotene at all tested concentration as well as vitamin B5 at 0.2× and 5× led to an increase in *Dialister* relative abundances in donor C. These increases were comparable to increases seen with the prebiotic FOS.

Human Study (FIG. 1C):

Administration of vitamin A, vitamin D3 and a combination of vitamin B2 and C for four weeks led to a an increase in *Dialister* relative abundance when compared to placebo. This was in contrast to what was observed for vitamin C.

The invention claimed is:

1. A method of increasing the population of *Dialister* spp. in the gut microbiome of an animal in need thereof, wherein the method comprises administering directly to the large intestine of the animal a population-increasing effective amount of a combination of Vitamin B2 and Vitamin C.

2. The method according to claim 1, wherein the animal is a human.

* * * * *